United States Patent [19]

Suzuki et al.

[11] Patent Number: 5,550,046
[45] Date of Patent: Aug. 27, 1996

[54] DNA ENCODING α-GLUCOSIDASE AND METHOD OF PRODUCING SAME BY GENETIC ENGINEERING

[75] Inventors: Yuzuru Suzuki, Shiga; Yukio Takii, Kyoto; Kazumi Yamamoto, Tsuruga; Yoshiaki Nishiya, Tsuruga; Atsushi Sogabe, Tsuruga; Yukihiro Sogabe, Tsuruga; Shigenori Emi, Tsuruga, all of Japan

[73] Assignee: Toyo Boseki Kabushiki Kaisha, Osaka, Japan

[21] Appl. No.: 39,777

[22] Filed: Mar. 22, 1993

[30]     Foreign Application Priority Data

Mar. 27, 1992  [JP]  Japan .................................. 4-101658
May 11, 1992  [JP]  Japan .................................. 4-117538

[51] Int. Cl.$^6$ .............................. C12N 9/28; C12N 9/26; C12N 15/56; C12N 15/63; C12N 5/10; C12N 1/00
[52] U.S. Cl. ........................ 435/202; 435/201; 435/243; 435/240.1; 435/252.3; 435/254.11; 536/23.2
[58] Field of Search ....................... 536/23.2; 435/320.1, 435/243, 240.1, 69.1, 832, 252.3, 254.11, 201, 202; 935/14

[56]              References Cited

U.S. PATENT DOCUMENTS 4,493,893  1/1985  Mielenz et al. ...................... 435/172.3

OTHER PUBLICATIONS

Enzyme Nomenclature 1984. New York:Academic Press, pp. 310–311.
Kapetzi et al. (1989) Yeast 5:11–24.
Takii et al. (1992) App. Microbiol. Biotechnol. 38 243–247.
Suzuki et al (1984) Biochin Biophys Acta 787 281–289.
McLaughlin J. R. et al. (1981) Journal of Biological Chemistry 256: 11283–11291.
Jordan A. et al. (1994) Journal of Bacteriology 176: 3420–3427.
Suzuki et al., "Production of Extracellular α–Glucosidase by a Thermophilic Bacillus Species", *Applied and Environmental Microbiol.*, 31, 6, 807–812 (1976).
American Type Culture Collection, *Catalogue of Bacteria and Bacteriophages*, Gherna et al., eds., 17th ed., p. 33 (1989).
Suzuki et al., "Assign," *Biochimica et Biophysica Acta*, 787, 281–289 (1984).

*Primary Examiner*—Robert A. Wax
*Assistant Examiner*—Gabriele E. Bugaisky
*Attorney, Agent, or Firm*—Leydig, Voit & Mayer, Ltd.

[57]              ABSTRACT

A protein having an α-glucosidase activity, wherein its N-terminal amino acid sequence is the sequence depicted in the Sequence Listing of the present invention at Sequence No: 1; a DNA having the genetic information of the protein having an α-glucosidase activity; a recombinant vector containing said DNA; a transformant transformed with said vector; and production of α-glucosidase comprising culture of said transformant in a medium so as to grow α-glucosidase, and harvesting said α-glucosidase. According to the present invention, α-glucosidase without contamination of amylase can be easily produced in high yields and in large amounts by genetic engineering.

4 Claims, 1 Drawing Sheet

FIG-1

P: PvuII
H: HincII
Sa: SacI
N: NruI
Sc: ScaI
X: XhoI

DNA ENCODING α-GLUCOSIDASE AND METHOD OF PRODUCING SAME BY GENETIC ENGINEERING

FIELD OF THE INVENTION

The present invention relates to an α-glucosidase usable for the production of starches, as well as for the determination of α-amylase present in body fluids which is clinically used as an index for the diagnoses of pancreatic diseases and salivary gland diseases; a DNA encoding protein having α-glucosidase activity; a recombinant vector containing said DNA; a transformant transformed with said vector; and production of α-glucosidase using said transformant.

BACKGROUND OF THE INVENTION

The organisms which produce α-glucosidase (α-D-glucoside glucohydrolase, EC 3.2.1.20) can be found widely in animals, plants, and microorganisms, and the α-glucosidases produced thereby show various characteristic properties depending on their source of origin. For example, the α-glucosidase originated from yeast is an enzyme scarcely affected by the sugar linked to non-reducing terminal glucose or aglycon of maltooligoglucoside derivatives as substrates, and is mainly used for the determination of α-amylase. The α-glucosidase in human urine or hog blood is known to scarcely show activity unless substrates have a glucose linked to non-reducing terminal glucose and said linkage is α-1,4-linkage.

With regard to the DNA sequence and the amino acid sequence of the α-glucosidase gene, there have been known those of human lysosomal α-glucosidase [Biochem. J. 272: 493–497 (1990)], fly α-glucosidase [J. Mol. Biol. 166 101–118 (1983)], mosquito α-glucosidase [Gene 75: 73–83 (1989)], yeast α-glucosidase [Gene 41: 75–84 (1986)], and so on. They are all derived from eukaryotes, and a prokaryote-originated gene useful for industrial production has not been found.

The α-glucosidase derived from the genus Bacillus is different from the one derived from yeast or animals hitherto known, and has superior heat resistance and wide substrate specificity permitting substantial reaction on maltotetraose, maltopentaose, etc. [Biochimica et Biophysica Acta: 787 281–289 (1984)].

Among strains belonging to the genus Bacillus, however, are those capable of producing α-amylase concurrently with α-glucosidase. The α-glucosidases obtained from those strains contain α-amylase even after purification, and occasionally cause error in determining amylase in body fluids.

SUMMARY OF THE INVENTION

Accordingly, it is an objective of the invention to clarify molecular structure of α-glucosidase by identifying the N-terminal amino acid sequence of α-glucosidase derived from the genus Bacillus, and to provide a means for producing said α-glucosidase in a pure form without contamination of α-amylase, at low costs and in large amounts by genetic engineering.

So as to achieve the objective mentioned above, the present inventors selected *Bacillus stearothermophilus* ATCC 12016 as an α-glucosidase producing cell, and, by the purification of its culture, successfully obtained an α-glucosidase preparation having a purity superior to the one reported in Biochimica et Biophysica Acta: 787 281–289 (1984) wherein an α-glucosidase was obtained by purifying the culture of a known strain, and the inventors identified its N-terminal amino acid sequence.

Furthermore, the present inventors have succeeded in the isolation of the α-glucosidase gene from chromosomal DNA extracted from *Bacillus stearothermophilus* ATCC 12016, and identified the entire structure of its DNA. Additionally, they have succeeded in producing said α-glucosidase in high yields by genetic engineering from a transformant which produces substantially no α-amylase, and made it possible to produce high purity α-glucosidase in large amounts at low costs.

DETAILED DESCRIPTION OF THE INVENTION

The present invention comprises a protein having α-glucosidase activity, wherein its N-terminal amino acid sequence is the sequence depicted in the Sequence Listing of the present invention as SEQ ID No: 1; a DNA encoding protein having α-glucosidase activity; a recombinant vector containing said DNA; a transformant transformed with said vector; and production of α-glucosidase comprising culture of said transformant in a medium so as to grow α-glucosidase, and harvesting said α-glucosidase.

In the present invention, the protein having α-glucosidase activity, wherein its N-terminal amino acid sequence is the sequence of SEQ ID No: 1, is a novel enzyme having an N-terminal amino acid sequence different from that of the α-glucosidase whose N-terminal amino acid sequence is known (e.g. those derived from human lysosomal, fly, mosquito, or yeast).

The protein having α-glucosidase activity in the present invention is an enzyme produced by *Bacillus stearothermophilus* ATCC 12016, and is different from known α-glucosidases in purity.

In the present invention, the microorganism belonging to the genus Bacillus is *Bacillus stearothermophilus*, which is exemplified by *Bacillus stearothermophilus* ATCC 12016.

The microorganisms belonging to the genus Bacillus may be cultured in a medium containing a carbon source, a nitrogen source, and inorganic ions, which may be further supplemented with nitrate, phosphate, etc. on demand. As the carbon source, usable are starch, hydrolyzed starch, molasses, etc. As the nitrogen source, usable are polypeptone, tryptone, meat extract, yeast extract, etc. It is preferred, although not required, that the culture is conducted under aerobic conditions with the pH and temperature of the medium appropriately adjusted. Culture should be continued until the α-glucosidase activity of the culture reaches its maximum level.

Harvesting of α-glucosidase from a culture comprises the following steps. The culture solution is centrifuged to collect cells, and then, an α-glucosidase-containing lysate is prepared by lysis. The lysis is suitably conducted by the treatment with a cell wall lytic enzyme such as lysozyme or β-glucanase, or physical lysis by ultrasonication or French press treatment.

The lysate thus obtained is subjected to, for example, ammonium sulfate precipitation fractionation, and after desalting, subjected to fractionation using a DEAE Sepharose CL- 6B column (Pharmacia LKB). Other columns may be used insofar as separation by ion exchange can be performed. Otherwise, this step may be skipped. The fractionated sample is subjected to High Performance Liquid Chromatography (HPLC, Pharmacia LKB) using Q-Sepharose HiLoad 16/10 (Pharmacia LKB), and then TSKgel Phenyl-5PW (Toso) for further purification. The purified product migrates as a single band on SDS polyacrylamide gel electrophoresis (SDS-PAGE). Note that the combination of column chromatographies is not limited to the one exemplified above, but may be altered optionally including the kind of the column to be used.

In the present invention, the purified standard α-glucosidase product was then applied to an amino acid sequencer, and the following N-terminal amino acid sequence (SEQ ID No: 1) was determined.

Met Lys Lys Thr Trp Trp Lys Glu Gly Val Ala Tyr Gln Ile Tyr

The protein of the present invention having α-glucosidase activity has the N-terminal amino acid sequence as depicted above, which is different from the N-terminal amino acid sequence of the α-glucosidase derived from human lysosomal, fly, mosquito or yeast.

The protein of the present invention having α-glucosidase activity has the amino acid sequence as depicted in the Sequence Listing as SEQ ID No: 3. One or more portions of said amino acid sequence may be replaced with other amino acid(s) or deleted, or other amino acid(s) may be inserted into the sequence so far as the α-glucosidase activity is maintained.

The DNA of the present invention encoding the protein having α-glucosidase activity (hereinafter also referred to as α-glucosidase gene) may be extracted from *Bacillus stearothermophilus*, or may be synthesized. The DNA sequence is, for example, a DNA sequence encoding the amino acid sequence as depicted in the Sequence Listing as SEQ ID No: 3, or a DNA having the nucleotide sequence as depicted in the Sequence Listing as SEQ ID No: 2. The DNA of the present invention includes those which underwent artificial mutation (e.g. replacement, deletion, insertion) at specific site(s) of the basal DNA by gene recombinant technique without changing basic characteristics of the α-glucosidase encoded by said DNA, occasionally for the purpose of improving the properties.

The recombinant vector for the DNA of the present invention is prepared by, for example, separating and purifying the DNA of *Bacillus stearothermophilus*, cleaving out DNA using ultrasonic waves or restriction enzyme, ligating said DNA with a linear expression vector by cyclization with DNA ligase at the blunt or cohesive ends of the both DNAs. The thus obtained recombinant vector is transfected into a replicable host, from which a microorganism carrying said recombinant vector is obtained by screening with the use of a marker of the vector and α-glucosidase activity as indices. The obtained microorganism is cultured, and from the cultured cells, a recombinant DNA vector is isolated and purified. Then, the α-glucosidase gene can be harvested from said recombinant vector.

A detailed explanation of DNA harvesting follows hereunder. The DNA derived from a gene donor microorganism is harvested as follows. A bacterium as mentioned above, which is the donor microorganism, is cultured, for example, in a liquid medium with aeration and agitation for about 1–3 days, after which the obtained culture is centrifuged, and cells are collected. By lysis, an α-glucosidase gene-containing lysate can be prepared. The lysis can be conducted by, for example, a treatment with a cell wall lyric enzyme, such as lysozyme or β-glucanase, with, where necessary, a concurrent use of other enzyme, such as a protease, or a surfactant, such as sodium lauryl sulfate. A physical lysis by freeze-thawing or French press treatment may be further combined with the lysis as described.

From the lysate thus obtained, DNA is isolated and purified by conventional methods, such as protein removal by phenol extraction, protease treatment, ribonuclease treatment, alcohol precipitation centrifugation, and the like, which may be combined as appropriate.

DNA isolated from microorganisms and then purified is cleaved by, for example, ultrasonic treatment or restriction enzyme treatment, with preference given to restriction enzyme treatment, using a restriction enzyme which acts on a specific nucleotide sequence, such as type II restriction enzymes (e.g. EcoRI, HindIII, BamHI), such that the ligation of a DNA fragment with a vector is facilitated.

As the vector, suitable is the one constructed for use in gene recombination from a phage or a plasmid capable of autonomic proliferation in a host.

As the phage, usable is, for example, λgt 10 or λgt 11 when *Escherichia coli* is used as a host.

As the plasmid, usable is, for example, pBR322 or pUG19 when *Escherichia coli* is used as a host, and pBU110 or pC194 when *Bacillus subtilis* is used as a host. In addition, a shuttle vector capable of autonomic proliferation in two or more hosts, including both Gram-negative hosts, such as *Escherichia coli*, and Gram-positive hosts, such as *Bacillus subtilis* may be used. Such a vector is preferably cleaved by the same restriction enzyme as used for the cleavage of DNA of the microorganism which is the α-glucosidase gene donor as mentioned above, to give a vector fragment. The method for ligating the microorganism DNA fragment with a vector fragment may be any method using a known DNA ligase, and is exemplified by a method comprising annealing cohesive ends of a microorganism DNA fragment and a vector fragment, and constructing a recombinant vector from the microorganism DNA fragment and the vector fragment with the use of a suitable DNA ligase. Where necessary, a recombinant vector may be prepared by a transfection into a host after annealing so that a DNA ligase in the host may be used.

As the host, any microorganism can be used as long as a recombinant vector is stable and capable of autonomic proliferation, and permits expression of the character of extraneous DNA, and usable are, for example, *Escherichia coli* W3110, *Escherichia coli* C600, or *Escherichia coli* JM109.

The recombinant vector is transferred into a host by, for example, when the host is a microorganism belonging to the genus Escherichia, transfection in the presence of a calcium ion, and when the host is a microorganism belonging to the genus Bacillus, by competent cell method or protoplast method, additionally with or without microinjection. It has been found that the microorganism (transformant) thus obtained can produce α-glucosidase stably and in a large amount by the culture thereof in a nutrient medium. The host microorganism to which the objective recombinant vector can be transfected is selected from the microorganisms capable of simultaneous expression of α-glucosidase and the drug tolerance marker of the vector carrying the objective DNA, and for example, a microorganism which can grow in a selective medium prepared according to the drug tolerance marker and produce α-glucosidase may be selected.

Preferably, 5-bromo-4-chloro-3-indolyl-α-D-glucopyranoside is added to a selective medium as a substrate for α-glucosidase, and a recombinant vector containing an α-glucosidase gene is screened using blue colony as an index.

The nucleotide sequence of the α-glucosidase gene obtained by the aforementioned steps was analyzed by the dideoxy method described in Science 214, 1205–1210 (1981), and the amino acid sequence of α-glucosidase was deduced from the nucleotide sequence. The N-terminal amino acid sequence of the α-glucosidase deduced from the nucleotide sequence was in perfect coincidence with the result of the analysis of the N-terminal amino acid sequence of the α-glucosidase derived from *Bacillus stearothermophilus* mentioned above. In this way, the recombinant vector containing the α-glucosidase gene once selected may be cleaved out from the transformed microorganism and transfected into other hosts with ease. Also, the DNA which is an α-glucosidase gene may be cleaved out from the recombinant vector containing the α-glucosidase gene with the use of a restriction enzyme, ligated with a vector fragment obtained by cleavage in a similar manner, and transfected into a host with ease.

Culture of a host microorganism may be conducted under the conditions selected in consideration of nutritional-physiological characteristics of the host. Generally, a liquid culture is selected, though culture with aeration and agitation is advantageous from an industrial aspect. The nutritive sources may be those usually employed for the culture of microorganisms. The carbon source may be any utilizable carbon compounds such as glucose, sucrose, lactose, maltose, fructose, molasses, and pyruvic acid. The nitrogen source may be any utilizable nitrogen compounds such as peptone, meat extract, yeast extract, hydrolyzed casein, and alkali extract of soybean. In addition to these, salts such as phosphate, carbonate, sulfate, magnesium, calcium, potassium, iron, manganese, and zinc, specific amino acids, specific vitamins, and so on may be used as necessary.

Culture temperature may be varied as appropriate within the range wherein cells can grow to produce α-glucosidase. In the case of *Escherichia coli*, the preferable temperature is from 20° C. to 42° C. While culture is carried out for somewhat different periods of time depending on culture conditions, it may be terminated at a suitable point when α-glucosidase has been produced in highest yields, which is normally from 12 to 48 hours. The pH of a medium may be varied as appropriate within the range wherein cells can grow to produce α-glucosidase, with preference given to a pH of about 6.0–8.0.

While the culture medium containing α-glucosidase-producing cells may be collected from a culture and used as it is, the α-glucosidase-containing solution and cells are, when α-glucosidase is contained in the culture medium, normally separated by conventional methods such as filtration, centrifugation, etc., and then used. When α-glucosidase is contained in cells, the cells are harvested by, for example, filtration or centrifugation of the obtained culture, and then destroyed by a mechanical method or an enzymatic method using lysozyme, etc., after which α-glucosidase is solubilized by adding a chelating agent such as EDTA and/or a surfactant as necessary, whereby α-glucosidase is obtained as an aqueous solution.

The thus-obtained solution containing α-glucosidase is subjected to, for example, concentration under reduced pressure, membrane concentration, salting out with ammonium sulfate, sodium sulfate, etc. or fractional precipitation using a hydrophilic organic solvent such as methanol, ethanol, acetone, etc., or the like to allow precipitation. Also, heat treatment and isoelectric treatment are effective means for purification. Purified α-glucosidase can be obtained by gel filtration using an adsorbent or a gel filtration agent, adsorption chromatography, ion exchange chromatography, affinity chromatography, or the like.

According to the present invention, the nucleotide sequence of the α-glucosidase gene, as well as the amino acid sequence of α-glucosidase have been clarified, and α-glucosidase without contamination of amylase can be easily produced in large amounts by genetic engineering.

The α-glucosidase obtained by the present invention has higher specific activity and higher purity than those conventionally known. Moreover, the α-glucosidase obtained by the present invention permits precise determination of α-amylase in body fluids, which is attributable to the absence of the contamination of α-amylase.

Still further, a novel α-glucosidase having higher activity or higher stability can be produced from the α-glucosidase gene of the present invention by various protein engineering methods.

The present invention is explained in more detail by way of the examples following.

In the examples, α-glucosidase activity was determined as follows.

An enzyme was reacted in 33.3 mM phosphate buffer (pH 6.8) containing 2 mM p-nitrophenyl-α-D-glucopyranoside at 60° C. for 20 minutes, and absorbance at 400 nm was determined. The amount of enzyme necessary for producing 1 μmol of p-nitrophenol per 1 minute under these conditions was taken as one unit of enzyme activity.

EXAMPLE 1

Determination of N-terminal amino acid sequence of α-glucosidase

The α-glucosidase-producing cell, *Bacillus stearothermophilus* ATCC 12016, was cultured in a 10 1-jar fermenter. The medium (pH 7.0) was supplemented with 2% soluble starch, 0.05% meat extract, 0.2% yeast extract, 0.3% $K_2HPO_4$ and 0.1% $KH_2PO_4$, and cultured with aeration and agitation at 60° C. for 10 hours.

The culture medium obtained (5.2 l) was centrifuged, and about 80 g of cells was separated. The cells were suspended in 50 mM phosphate buffer, pH 7.0, lysed in Dyno Mill to give about 2 l of a cell lysate. The α-glucosidase activity at this time was 5.8 U/ml. After sulfate fractionation, the lysate was desalted on Sephadex G-25 (Pharmacia LKB). The specific activity at this time was 4.0 U/mg.

The desalted solution was applied to a DEAE Sepharose CL-6B column equilibrated with 50 mM phosphate buffer, pH 7.0, and the adsorbed fraction was eluted by 0–0.3M NaCl gradient. Thereafter, the obtained fraction was desalted again on Sephadex G-25. The desalted solution was subjected to HPLC on Q Sepharose HiLoad 16/10 column for ion exchange chromatography, and then to hydrophobic chromatography using a TSKgel Phenyl-5PW column to give a purified α-glucosidase preparation. The specific activity of the α-glucosidase preparation was 150 U/mg, and activity yield was 13%. The α-glucosidase preparation was subjected to SDS-PAGE. This preparation migrated as a single band and had a molecular weight of about 65,000.

The purifications so far conducted are summarized in Table 1.

TABLE 1

α-glucosidase purification

| Steps | total activity (U) | specific activity (U/mg) | yield (%) | α-amylase content (%) |
|---|---|---|---|---|
| cell lysis | 10967 | 0.24 | 100 | 19.3 |
| sulfate fractionation | 12100 | 1.88 | 110 | 15.4 |
| DEAE Sepharose | 10285 | 5.50 | 94 | $5.2 \times 10^{-3}$ |
| Q Sepharose | 5347 | 87.5 | 49 | $1.2 \times 10^{-3}$ |
| Phenyl-5PW | 1390 | 150.0 | 13 | $5.6 \times 10^{-5}$ |

The purified α-glucosidase preparation was analyzed by an amino acid sequencer, and the N-terminal amino acid sequence of α-glucosidase shown in the Sequence Listing as SEQ ID No: 1 was determined.

EXAMPLE 2

Separation of chromosomal DNA

The chromosomal DNA of *Bacillus stearothermophilus* ATCC 12016 was isolated by the following method. This cell line was subjected to a shaking culture in an ordinary bouillon medium (150 ml) at 60° C. overnight, and centrifuged (8000 rpm, 10 minutes) to collect cells. The cells were suspended in 5 ml of a solution containing 10% sucrose, 50 mM Tris-HCl buffer (pH 8.0), and 50 mM EDTA, after which 1 ml of a lysozyme solution (10 mg/ml) was added thereto, and the mixture was incubated at 37° C. for 15 minutes, followed by addition of 10% SDS (sodium dodecyl sulfate, 1 ml). To the suspension was added an equivalent amount of a chloroform-phenol solution (1:1), and the mixture was stirred. Then, the mixture was centrifuged at 10,000 rpm for 3 minutes to divide same into a water layer and a solvent layer, and the water layer was separated. A two-fold amount of ethanol was gently layered onto the water layer, and DNA was isolated by slowly stirring the mixture with a glass rod to allow the DNA to wind around the glass rod, which was then dissolved in a solution of 10 mM Tris-HCl (pH 8.0) and 1 mM EDTA (hereinafter abbreviated as TE). After treating the solution with an equivalent amount of chloroform-phenol, the water layer was separated by centrifugation. A two-fold amount of ethanol was added thereto, and the DNA was again isolated in the same manner as above and dissolved in 2 ml of TE.

The competent cells of *Escherichia coli* JM109 were prepared by the method of Hanahan, and used as hosts for library construction.

EXAMPLE 3

Preparation of DNA fragment containing a gene encoding α-glucosidase, and recombinant vector containing said DNA fragment The DNA (1 μg) obtained in Example 2 was reacted with 10 units of the restriction enzyme AvaI (manufactured by Toyo Boseki K.K.) at 37° C. for 1 hour to complete restriction. In a similar manner, the DNA was reacted with 0.5 μg of pUC19 cleaved with AvaI, in the presence of 1 unit of T4-DNA ligase (manufactured by Toyo Boseki K.K.) at 16° C. for 12 hours to ligate the DNA. The DNA thus ligated was used to transform the competent cells of *Escherichia coli* JM109. A colony of about $1 \times 10^6$ transformed cells was obtained per 1 μg of the DNA used. The obtained colonies were cultured in an LB medium (1% polypeptone, 0.5% yeast extract, 0.5% sodium chloride) supplemented with 50 μg/ml ampicillin and 0.01% 5-bromo-4-chloro- 3-indolyl-α-glucopyranoside at 37° C. for 18 hours, and the recombinant DNA containing the α-glucosidase gene was screened using blue colony as an index.

Figure 1:
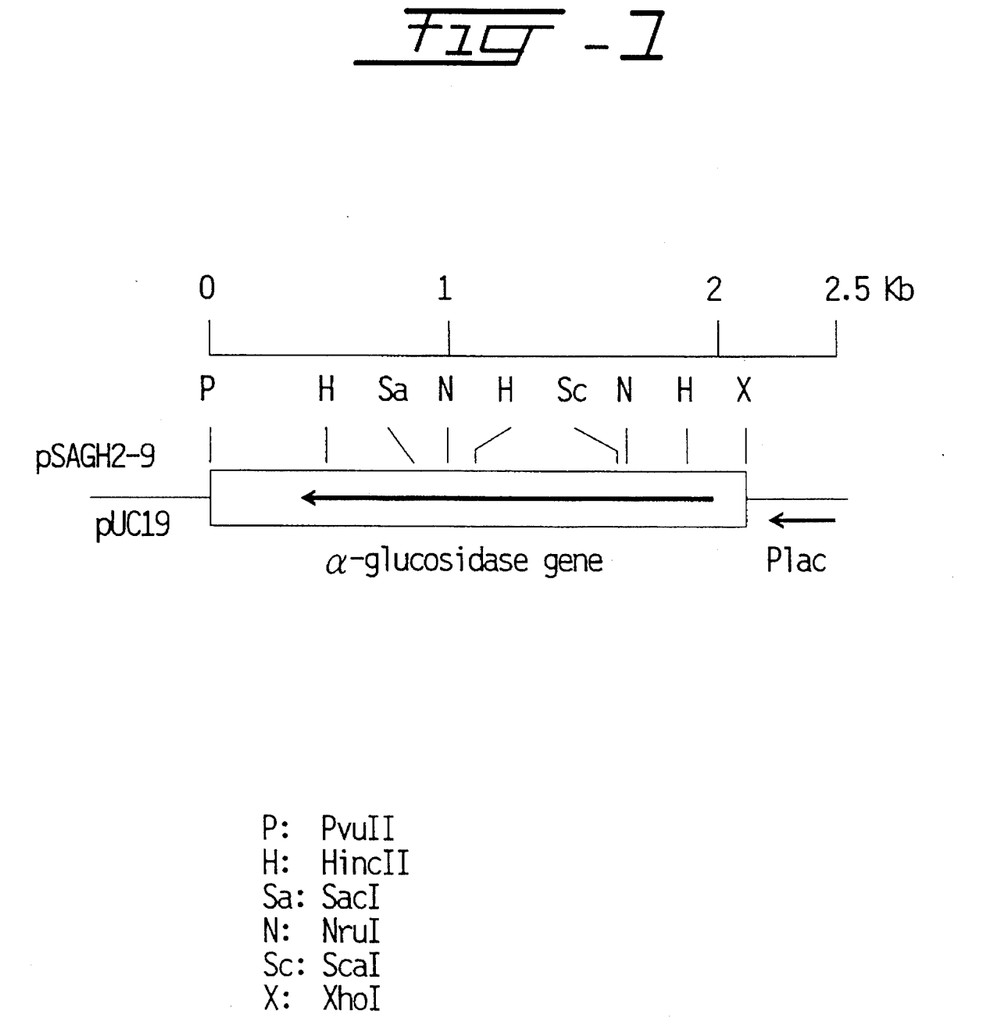
FIG. 1 is a restriction enzyme map of a DNA insert in pSAGH2-9.

As a result, one colony displaying a blue color was obtained out of about 3000 colonies. The plasmid therein contained an about 5.4 kbp DNA fragment insert, and this plasmid was named pSAGH1. Then, the DNA fragment insert was cleaved from pSAGH1 by various restriction enzymes, subcloned into pUC19 to yield pSAGH2-9 containing an about 2.2 kbp DNA fragment insert, with which *Escherichia coli* JM109 was transformed. The restriction enzyme map of the DNA insert of pSAGH2-9 is shown in FIG. 1.

EXAMPLE 4

Determination of nucleotide sequence

The about 2.2 kbp DNA fragment insert of pSAGH2-9 was cleaved with various restriction enzymes, and subclones were prepared. The various subclones were prepared into a single-stranded DNA by conventional methods, and the single-stranded DNA was analyzed by SEQUENASE VERSION 2.0 7-deaza dGTP kit (manufactured by Toyo Boseki K.K.) to determine its nucleotide sequence. The nucleotide sequence and the amino acid sequence are shown in SEQ ID NO: 2.

EXAMPLE 5

Production of α-glucosidase

The aforementioned LB medium (6 l) was dispensed into a 10 l-jar fermenter, autoclaved at 121° C. for 15 minutes, allowed to cool, 6 ml of 50 mg/ml ampicillin (manufactured by Nacalai Tesque) and 200 mM IPTG which had been separately sterilized by filtration, were added. Into this medium was inoculated 60 ml of a culture medium of *Escherichia coli* JM109 (pSAGH2-9) which had been previously subjected to shaking culture at 37° C. for 18 hours in a medium having the same composition as above, and the medium was subjected to culture with aeration and agitation at 37° C. for 18 hours. The α-glucosidase activity upon termination of the culture was 12.5 U/ml. The culture medium (6 l) was centrifuged to collect cells, and the cells were suspended in 200 ml of 50 mM phosphate buffer (pH 7.0). The cells were lysed by a conventional method using Daino Mill, and centrifuged at 15,000 rpm for 20 minutes to give a crude enzyme solution of α-glucosidase. This crude solution was treated with protamine to remove nucleic acid, and subjected to fractionation using ammonium sulfate. The precipitate was dissolved in 50 ml of 50 mM phosphate buffer (pH 7.0), and heated at 55° C. for 16 hours. The resultant solution was desalted on Sephadex G-25, and subjected to DEAE Sepharose CL-6B chromatography to give an α-glucosidase active fraction.

The α-glucosidase fraction after the DEAE Sepharose chromatography showed a single band on SDS-PAGE, with a specific activity of 187 U/mg and an activity yield of 70.5%. The enzyme properties of the α-glucosidase obtained from a transformant were as follows: molecular weight 65,000, isoelectric point 5.2, optimal pH 6–7, heat resistance not more than 60° C. (pH 7.0, 15 minutes treatment), and optimal temperature 60° C. The purifications so far conducted are summarized in Table 2.

TABLE 2

| | α-glucosidase purification | | | |
|---|---|---|---|---|
| Steps | total activity (U) | specific activity (U/mg) | yield (%) | α-amylase content (%) |
| cell lysis | 74850 | 7.13 | 100 | $3.1 \times 10^{-3}$ |
| sulfate fractionation | 89070 | 59.0 | 119 | $2.4 \times 10^{-3}$ |
| heat treatment | 65942 | 92.3 | 88.1 | $5.8 \times 10^{-5}$ |

TABLE 2-continued

| | α-glucosidase purification | | | |
|---|---|---|---|---|
| Steps | total activity (U) | specific activity (U/mg) | yield (%) | α-amylase content (%) |
| DEAE Sepharose | 52767 | 187.0 | 70.5 | $1.0 \times 10^{-5}$ |

Compared with the results of Table 1, an about 38 times greater amount of α-glucosidase was obtained at higher purity by the same culture scale but by easier purification method.

What is claimed:

1. An isolated and purified DNA comprising a nucleotide sequence encoding α-glucosidase, wherein said DNA has the nucleotide sequence of SEQ ID NO:2.

2. A recombinant expression vector containing an exogenous DNA sequence encoding α-glucosidase, wherein said vector is capable of expressing α-glucosidase in a transformant and wherein said DNA has the nucleotide sequence of SEQ ID NO:2.

3. A transformed cell capable of expressing α-glucosidase, wherein said transformed cell is obtained by transforming a microorganism with the vector of claims 2.

4. A method for producing α-glucosidase comprising the steps of:
(a) cultivating a transformed cell harboring an expression vector of claim 2 in a medium to produce α-glucosidase, wherein said α-glucosidase has the amino acid sequence of SEQ ID NO:2; and
(b) harvesting said α-glucosidase.

* * * * *

UNITED STATES PATENT AND TRADEMARK OFFICE
CERTIFICATE OF CORRECTION

PATENT NO. : 5,550,046
DATED : August 27, 1996
INVENTOR(S) : Suzuki et al.

It is certified that error appears in the above-identified patent and that said Letters Patent is hereby corrected as shown below:

In Column 4, line 23: "pUG19" should read --pUC19--.

Signed and Sealed this

Eighteenth Day of February, 1997

BRUCE LEHMAN

Attest:

*Attesting Officer*          *Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal fragment     ( v i ) ORIGINAL SOURCE:
        ( A ) ORGANISM: Bacillus stearothermophilus
        ( B ) STRAIN: ATCC12016

( x i ) SEQUENCE DESCRIPTION: SEQ ID NO:1:

```
Met   Lys   Lys   Thr   Trp   Trp   Lys   Glu   Gly   Val   Ala   Tyr   Gln   Ile   Tyr
 1                       5                           10                          15
```

( 2 ) INFORMATION FOR SEQ ID NO:2:

( i ) SEQUENCE CHARACTERISTICS:
        ( A ) LENGTH: 2074 base pairs
        ( B ) TYPE: nucleic acid
        ( C ) STRANDEDNESS: double
        ( D ) TOPOLOGY: linear     ( i i ) MOLECULE TYPE: DNA (genomic)

( i i i ) HYPOTHETICAL: YES

( i v ) ANTI-SENSE: NO

( v i ) ORIGINAL SOURCE:
        ( A ) ORGANISM: Bacillus stearothermophilus
        ( B ) STRAIN: ATCC12016

( v i i ) IMMEDIATE SOURCE:
        ( A ) LIBRARY: genomic     ( i x ) FEATURE:
        ( A ) NAME/KEY: CDS
        ( B ) LOCATION: 199..1863

( x i ) SEQUENCE DESCRIPTION: SEQ ID NO:2:

```
CTCGAGGTGG   TATATCACAA   TTTAAAAATT   TACGAAGCGA   GCCGCGCAAC   CGGTGAGTGA         60
```

-continued

```
CCAGTTGTCA AACCCAGCCGT TTGGCAGGAG CGTGCAGCCC CGCCAAACGG CTGTTTTTTG                    120

AGAAAAAGAG AAGTTGTTTA CCGCACCAAT ATAGTGTACA GTTAATAGTG AAAACGTGTG                    180

CACAAGGAGG AGGCAGCC TTG AAA AAA ACA TGG TGG AAA GAA GGC GTT GCG                      231
                    Leu Lys Lys Thr Trp Trp Lys Glu Gly Val Ala
                     1       5                       10

TAT CAA ATT TAT CCT CGC AGC TTT ATG GAT GCC AAC GGC GAC GGC ATC                      279
Tyr Gln Ile Tyr Pro Arg Ser Phe Met Asp Ala Asn Gly Asp Gly Ile
            15              20              25

GGT GAT CTT CGC GGC ATC ATC GAA AAG CTG GAT TAT TTG GTG GAG CTT                      327
Gly Asp Leu Arg Gly Ile Ile Glu Lys Leu Asp Tyr Leu Val Glu Leu
        30              35              40

GGA GTC GAC ATC GTT TGG ATT TGT CCG ATT TAC CGG TCG CCG AAC GCT                      375
Gly Val Asp Ile Val Trp Ile Cys Pro Ile Tyr Arg Ser Pro Asn Ala
    45              50              55

GAT AAT GGA TAT GAC ATC AGC GAC TAT TAT GCC ATT ATG GAT GAG TTT                      423
Asp Asn Gly Tyr Asp Ile Ser Asp Tyr Tyr Ala Ile Met Asp Glu Phe
60              65              70                              75

GGA ACG ATG GAT GAC TTC GAT GAA TTG CTT GCC CAA GCC CAT CGG CGC                      471
Gly Thr Met Asp Asp Phe Asp Glu Leu Leu Ala Gln Ala His Arg Arg
                80              85                      90

GGG TTG AAA ATC ATT TTG GAT TTG GTC ATC AAT CAT ACG AGT GAT GAG                      519
Gly Leu Lys Ile Ile Leu Asp Leu Val Ile Asn His Thr Ser Asp Glu
        95              100                     105

CAT CCG TGG TTT ATC GAA TCG CGG TCA TCG CGA GAC AAT CCG AAG CGC                   567
   His Pro Trp Phe Ile Glu Ser Arg Ser Ser Arg Asp Asn Pro Lys Arg
           110             115                     120

GAC TGG TAC ATT TGG CGC GAC GGC AAA GAT GGG CGC GAA CCG AAC AAC                      615
Asp Trp Tyr Ile Trp Arg Asp Gly Lys Asp Gly Arg Glu Pro Asn Asn
    125             130                     135

TGG GAA AGC ATT TTC GGC GGC TCG GCA TGG CAG TAT GAC GAG CGG ACG                      663
Trp Glu Ser Ile Phe Gly Gly Ser Ala Trp Gln Tyr Asp Glu Arg Thr
140             145                     150                 155

GGT CAG TAC TAT TTA CAT CTT TTC GAT GTG AAA CAG CCC GAT TTG AAC                      711
Gly Gln Tyr Tyr Leu His Leu Phe Asp Val Lys Gln Pro Asp Leu Asn
            160                 165                     170

TGG GAA AAC AGC GAG GTG CGC CAA GCG CTG TAT GAC ATG ATC AAC TGG                      759
Trp Glu Asn Ser Glu Val Arg Gln Ala Leu Tyr Asp Met Ile Asn Trp
                175                 180                 185

TGG CTG GAT AAA GGC ATC GAC GGC TTT CGC ATC GAC GCG ATT TCC CAC                      807
Trp Leu Asp Lys Gly Ile Asp Gly Phe Arg Ile Asp Ala Ile Ser His
        190                 195                 200

ATT AAG AAA AAG CCG GGT CTT CCC GAT TTG CCA AAT CCG AAG GGG CTG                      855
Ile Lys Lys Lys Pro Gly Leu Pro Asp Leu Pro Asn Pro Lys Gly Leu
    205                 210                 215

AAG TAC GTG CCG TCA TTT GCT GCG CAC ATG AAC CAG CCA GGG ATT ATG                      903
Lys Tyr Val Pro Ser Phe Ala Ala His Met Asn Gln Pro Gly Ile Met
220                 225                 230                 235

GAG TAT TTG CGA GAG TTG AAA GAG CAA ACG TTT GCA CGA TAT GAC ATT                      951
Glu Tyr Leu Arg Glu Leu Lys Glu Gln Thr Phe Ala Arg Tyr Asp Ile
            240                 245                 250

ATG ACG GTC GGC GAG GCG AAC GGA GTA ACG GTT GAT GAG GCC GAA CAA                      999
Met Thr Val Gly Glu Ala Asn Gly Val Thr Val Asp Glu Ala Glu Gln
                255                 260                 265

TGG GTC GGG GAA GAA AAC GGC GTG TTT CAT ATG ATT TTT CAG TTC GAG                     1047
Trp Val Gly Glu Glu Asn Gly Val Phe His Met Ile Phe Gln Phe Glu
        270                 275                 280

CAT TTA GGG CTT TGG AAA AGG AAA GCA GAT GGT TCG ATC GAT GTC CGC                     1095
His Leu Gly Leu Trp Lys Arg Lys Ala Asp Gly Ser Ile Asp Val Arg
    285                 290                 295
```

| | | | | | | | | | | | | | | | | |
|---|---|---|---|---|---|---|---|---|---|---|---|---|---|---|---|---|
| CGG | CTG | AAG | CGG | ACG | TTG | ACG | AAA | TGG | CAA | AAA | GGA | TTG | GAA | AAT | CGT | 1143 |
| Arg | Leu | Lys | Arg | Thr | Leu | Thr | Lys | Trp | Gln | Lys | Gly | Leu | Glu | Asn | Arg | |
| 300 | | | | | 305 | | | | 310 | | | | | | 315 | |
| GGG | TGG | AAC | GCG | CTC | TTT | TTG | GAA | AAC | CAC | GAC | TTG | CCT | CGA | TCG | GTG | 1191 |
| Gly | Trp | Asn | Ala | Leu | Phe | Leu | Glu | Asn | His | Asp | Leu | Pro | Arg | Ser | Val | |
| | | | | 320 | | | | | 325 | | | | | 330 | | |
| TCG | ACG | TGG | GGC | AAT | GAC | CGC | GAG | TAT | TGG | GCG | GAG | AGC | GCG | AAG | GCG | 1239 |
| Ser | Thr | Trp | Gly | Asn | Asp | Arg | Glu | Tyr | Trp | Ala | Glu | Ser | Ala | Lys | Ala | |
| | | | 335 | | | | | 340 | | | | | 345 | | | |
| CTT | GGC | GCG | CTC | TAC | TTT | TTC | ATG | CAA | GGG | ACG | CCG | TTC | ATT | TAC | CAA | 1287 |
| Leu | Gly | Ala | Leu | Tyr | Phe | Phe | Met | Gln | Gly | Thr | Pro | Phe | Ile | Tyr | Gln | |
| | | 350 | | | | | 355 | | | | | 360 | | | | |
| GGG | CAA | GAG | ATC | GGG | ATG | ACG | AAC | GTG | CAA | TTC | TCC | GAC | ATT | CGC | GAT | 1335 |
| Gly | Gln | Glu | Ile | Gly | Met | Thr | Asn | Val | Gln | Phe | Ser | Asp | Ile | Arg | Asp | |
| | 365 | | | | | 370 | | | | | 375 | | | | | |
| TAC | CGC | GAT | GTC | GCT | GCC | TTG | CGT | CTG | TAT | GAG | CTC | GAA | CGG | GCG | AAC | 1383 |
| Tyr | Arg | Asp | Val | Ala | Ala | Leu | Arg | Leu | Tyr | Glu | Leu | Glu | Arg | Ala | Asn | |
| 380 | | | | | 385 | | | | 390 | | | | | | 395 | |
| GGC | CGG | ACG | CAT | GAG | GAA | GTG | ATG | AAG | ATC | ATT | TGG | AAA | ACC | GGG | CGC | 1431 |
| Gly | Arg | Thr | His | Glu | Glu | Val | Met | Lys | Ile | Ile | Trp | Lys | Thr | Gly | Arg | |
| | | | | 400 | | | | | 405 | | | | | 410 | | |
| GAC | AAC | TCG | CGC | ACC | CCG | ATG | CAA | TGG | TCT | GAT | GCC | CCG | AAT | GCA | GGG | 1479 |
| Asp | Asn | Ser | Arg | Thr | Pro | Met | Gln | Trp | Ser | Asp | Ala | Pro | Asn | Ala | Gly | |
| | | | 415 | | | | | 420 | | | | | 425 | | | |
| TTT | ACG | ACT | GGC | ACG | CCA | TGG | ATC | AAG | GTG | AAC | GAA | AAC | TAT | CGT | ACG | 1527 |
| Phe | Thr | Thr | Gly | Thr | Pro | Trp | Ile | Lys | Val | Asn | Glu | Asn | Tyr | Arg | Thr | |
| | | 430 | | | | | 435 | | | | | 440 | | | | |
| ATC | AAT | GTC | GAG | GCC | GAG | CGG | CGC | GAC | CCG | AAC | TCA | GTA | TGG | TCG | TTT | 1575 |
| Ile | Asn | Val | Glu | Ala | Glu | Arg | Arg | Asp | Pro | Asn | Ser | Val | Trp | Ser | Phe | |
| | 445 | | | | | 450 | | | | | 455 | | | | | |
| TAT | CGA | CAA | ATG | ATT | CAG | CTT | CGG | AAA | GCG | AAC | GAG | CTG | TTT | GTT | TAC | 1623 |
| Tyr | Arg | Gln | Met | Ile | Gln | Leu | Arg | Lys | Ala | Asn | Glu | Leu | Phe | Val | Tyr | |
| 460 | | | | | 465 | | | | 470 | | | | | | 475 | |
| GGA | GCG | TAC | GAT | CTG | CTT | TTG | GAA | AAT | CAC | CCA | TCC | ATT | TAC | GCG | TAC | 1671 |
| Gly | Ala | Tyr | Asp | Leu | Leu | Leu | Glu | Asn | His | Pro | Ser | Ile | Tyr | Ala | Tyr | |
| | | | | 480 | | | | | 485 | | | | | 490 | | |
| ACA | AGA | ACG | CTT | GGC | CGC | GAT | CGG | GCG | CTT | ATC | ATT | GTC | AAC | GTA | TCC | 1719 |
| Thr | Arg | Thr | Leu | Gly | Arg | Asp | Arg | Ala | Leu | Ile | Ile | Val | Asn | Val | Ser | |
| | | | 495 | | | | | 500 | | | | | 505 | | | |
| GAT | CGT | CCT | TCA | CTT | TAC | CGC | TAT | GAC | GGC | TTC | CGC | CTT | CAG | TCA | AGC | 1767 |
| Asp | Arg | Pro | Ser | Leu | Tyr | Arg | Tyr | Asp | Gly | Phe | Arg | Leu | Gln | Ser | Ser | |
| | | 510 | | | | | 515 | | | | | 520 | | | | |
| GAT | TTG | GCG | CTT | TCG | AAC | TAC | CCG | GTC | CGT | CCG | CAT | AAA | AAT | GCG | ACG | 1815 |
| Asp | Leu | Ala | Leu | Ser | Asn | Tyr | Pro | Val | Arg | Pro | His | Lys | Asn | Ala | Thr | |
| | 525 | | | | | 530 | | | | | 535 | | | | | |
| CGT | TTT | AAG | CTG | AAG | CCG | TAC | GAG | GCG | CGC | GTA | TAC | ATC | TGG | AAA | GAA | 1863 |
| Arg | Phe | Lys | Leu | Lys | Pro | Tyr | Glu | Ala | Arg | Val | Tyr | Ile | Trp | Lys | Glu | |
| 540 | | | | | 545 | | | | 550 | | | | | | 555 | |

TAAGAAGGAA TTTGCCTTTC CGTGTGGAAT AAATGCATAC GGAAGGGAGA TGATCAACAT 1923

GGCAACGGTC GATCCGATTC GCTACCCGAT CGGAACGTTT CAAGCGCCGC AGCAGTTTGA 1983

GGCTGGGGAG GTGCAAGAGT GGATTGCTGC CATCCGCGGG TTGCCGAGCG ACTTAAGAAC 2043

CGCTGTTTCC GGCTTGAACG ATGAGCAGCT G 2074

( 2 ) INFORMATION FOR SEQ ID NO:3:

( i ) SEQUENCE CHARACTERISTICS:
        ( A ) LENGTH: 555 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Leu | Lys | Lys | Thr | Trp | Trp | Lys | Glu | Gly | Val | Ala | Tyr | Gln | Ile | Tyr | Pro |
| 1 | | | | 5 | | | | | 10 | | | | | 15 | |

| Arg | Ser | Phe | Met | Asp | Ala | Asn | Gly | Asp | Gly | Ile | Gly | Asp | Leu | Arg | Gly |
| | | | 20 | | | | 25 | | | | | 30 | | | |

| Ile | Ile | Glu | Lys | Leu | Asp | Tyr | Leu | Val | Glu | Leu | Gly | Val | Asp | Ile | Val |
| | | | 35 | | | | 40 | | | | | 45 | | | |

| Trp | Ile | Cys | Pro | Ile | Tyr | Arg | Ser | Pro | Asn | Ala | Asp | Asn | Gly | Tyr | Asp |
| | | 50 | | | | 55 | | | | | 60 | | | | |

| Ile | Ser | Asp | Tyr | Tyr | Ala | Ile | Met | Asp | Glu | Phe | Gly | Thr | Met | Asp | Asp |
| 65 | | | | | 70 | | | | 75 | | | | | | 80 |

| Phe | Asp | Glu | Leu | Leu | Ala | Gln | Ala | His | Arg | Arg | Gly | Leu | Lys | Ile | Ile |
| | | | | 85 | | | | | 90 | | | | | 95 | |

| Leu | Asp | Leu | Val | Ile | Asn | His | Thr | Ser | Asp | Glu | His | Pro | Trp | Phe | Ile |
| | | | 100 | | | | 105 | | | | | 110 | | | |

| Glu | Ser | Arg | Ser | Ser | Arg | Asp | Asn | Pro | Lys | Arg | Asp | Trp | Tyr | Ile | Trp |
| | | 115 | | | | | 120 | | | | | 125 | | | |

| Arg | Asp | Gly | Lys | Asp | Gly | Arg | Glu | Pro | Asn | Asn | Trp | Glu | Ser | Ile | Phe |
| | 130 | | | | 135 | | | | | 140 | | | | | |

| Gly | Gly | Ser | Ala | Trp | Gln | Tyr | Asp | Glu | Arg | Thr | Gly | Gln | Tyr | Tyr | Leu |
| 145 | | | | | 150 | | | | | 155 | | | | | 160 |

| His | Leu | Phe | Asp | Val | Lys | Gln | Pro | Asp | Leu | Asn | Trp | Glu | Asn | Ser | Glu |
| | | | | 165 | | | | | 170 | | | | | 175 | |

| Val | Arg | Gln | Ala | Leu | Tyr | Asp | Met | Ile | Asn | Trp | Trp | Leu | Asp | Lys | Gly |
| | | | 180 | | | | 185 | | | | | 190 | | | |

| Ile | Asp | Gly | Phe | Arg | Ile | Asp | Ala | Ile | Ser | His | Ile | Lys | Lys | Lys | Pro |
| | | 195 | | | | | 200 | | | | | 205 | | | |

| Gly | Leu | Pro | Asp | Leu | Pro | Asn | Pro | Lys | Gly | Leu | Lys | Tyr | Val | Pro | Ser |
| | 210 | | | | 215 | | | | | 220 | | | | | |

| Phe | Ala | Ala | His | Met | Asn | Gln | Pro | Gly | Ile | Met | Glu | Tyr | Leu | Arg | Glu |
| 225 | | | | | 230 | | | | | 235 | | | | | 240 |

| Leu | Lys | Glu | Gln | Thr | Phe | Ala | Arg | Tyr | Asp | Ile | Met | Thr | Val | Gly | Glu |
| | | | | 245 | | | | | 250 | | | | | 255 | |

| Ala | Asn | Gly | Val | Thr | Val | Asp | Glu | Ala | Gln | Trp | Val | Gly | Glu | Glu |
| | | | 260 | | | | 265 | | | | | 270 | | | |

| Asn | Gly | Val | Phe | His | Met | Ile | Phe | Gln | Phe | Glu | His | Leu | Gly | Leu | Trp |
| | | 275 | | | | | 280 | | | | | 285 | | | |

| Lys | Arg | Lys | Ala | Asp | Gly | Ser | Ile | Asp | Val | Arg | Arg | Leu | Lys | Arg | Thr |
| | 290 | | | | 295 | | | | | 300 | | | | | |

| Leu | Thr | Lys | Trp | Gln | Lys | Gly | Leu | Glu | Asn | Arg | Gly | Trp | Asn | Ala | Leu |
| 305 | | | | | 310 | | | | | 315 | | | | | 320 |

| Phe | Leu | Glu | Asn | His | Asp | Leu | Pro | Arg | Ser | Val | Ser | Thr | Trp | Gly | Asn |
| | | | | 325 | | | | | 330 | | | | | 335 | |

| Asp | Arg | Glu | Tyr | Trp | Ala | Glu | Ser | Ala | Lys | Ala | Leu | Gly | Ala | Leu | Tyr |
| | | | 340 | | | | 345 | | | | | 350 | | | |

| Phe | Phe | Met | Gln | Gly | Thr | Pro | Phe | Ile | Tyr | Gln | Gly | Gln | Glu | Ile | Gly |
| | | 355 | | | | | 360 | | | | | 365 | | | |

| Met | Thr | Asn | Val | Gln | Phe | Ser | Asp | Ile | Arg | Asp | Tyr | Arg | Asp | Val | Ala |
| | 370 | | | | 375 | | | | | 380 | | | | | |

| Ala | Leu | Arg | Leu | Tyr | Glu | Leu | Glu | Arg | Ala | Asn | Gly | Arg | Thr | His | Glu |
| 385 | | | | | 390 | | | | | 395 | | | | | 400 |

| | | | | | | | | | | | | | | | |
|---|---|---|---|---|---|---|---|---|---|---|---|---|---|---|---|
| Glu | Val | Met | Lys | Ile 405 | Ile | Trp | Lys | Thr | Gly 410 | Arg | Asp | Asn | Ser | Arg 415 | Thr |
| Pro | Met | Gln | Trp 420 | Ser | Asp | Ala | Pro | Asn 425 | Ala | Gly | Phe | Thr | Thr 430 | Gly | Thr |
| Pro | Trp | Ile 435 | Lys | Val | Asn | Glu | Asn 440 | Tyr | Arg | Thr | Ile | Asn 445 | Val | Glu | Ala |
| Glu | Arg 450 | Arg | Asp | Pro | Asn | Ser 455 | Val | Trp | Ser | Phe | Tyr 460 | Arg | Gln | Met | Ile |
| Gln 465 | Leu | Arg | Lys | Ala | Asn 470 | Glu | Leu | Phe | Val | Tyr 475 | Gly | Ala | Tyr | Asp | Leu 480 |
| Leu | Leu | Glu | Asn | His 485 | Pro | Ser | Ile | Tyr | Ala 490 | Tyr | Thr | Arg | Thr | Leu 495 | Gly |
| Arg | Asp | Arg | Ala 500 | Leu | Ile | Ile | Val | Asn 505 | Val | Ser | Asp | Arg | Pro 510 | Ser | Leu |
| Tyr | Arg | Tyr 515 | Asp | Gly | Phe | Arg | Leu 520 | Gln | Ser | Ser | Asp | Leu 525 | Ala | Leu | Ser |
| Asn | Tyr 530 | Pro | Val | Arg | Pro | His 535 | Lys | Asn | Ala | Thr | Arg 540 | Phe | Lys | Leu | Lys |
| Pro 545 | Tyr | Glu | Ala | Arg | Val 550 | Tyr | Ile | Trp | Lys | Glu 555 | | | | | |